United States Patent [19]
Quintanilla et al.

[11] Patent Number: 5,188,454
[45] Date of Patent: Feb. 23, 1993

[54] LAMP HANDLE COVER SYSTEM FOR SURGICAL LAMPS

[75] Inventors: Roberto Quintanilla; Alberto Quintanilla, both of El Paso, Tex.

[73] Assignee: Transmedical Corporation, San Antonio, Tex.

[21] Appl. No.: 693,697

[22] Filed: Apr. 30, 1991

Related U.S. Application Data

[63] Continuation of Ser. No. 585,290, Sep. 19, 1990, Pat. No. 5,036,446, which is a continuation of Ser. No. 235,978, Aug. 27, 1988, abandoned.

[51] Int. Cl.5 .............................................. F21L 15/12
[52] U.S. Cl. .................................... 362/399; 362/376; 362/400; 362/804
[58] Field of Search ............... 362/109, 376, 399, 400, 362/457, 458, 804; 16/114 R, DIG. 24, DIG. 25; 128/395, 396; 206/570

[56] References Cited

U.S. PATENT DOCUMENTS

| | | | |
|---|---|---|---|
| 3,887,801 | 6/1975 | Ilzig et al. | 362/33 |
| 4,559,671 | 12/1985 | Andrews et al. | 16/DIG. 19 X |
| 4,605,124 | 8/1986 | Sandel et al. | 362/399 X |
| 5,036,446 | 7/1991 | Quintanilla et al. | 362/399 |

Primary Examiner—Stephen F. Husar
Attorney, Agent, or Firm—Donald R. Comuzzi

[57] ABSTRACT

The lamp handle cover system for surgical lamps includes a semi-permanent, non-disposal surgical lamp handle and its accessory component, a sterile disposable semi-flexible handle cover, which, in combination, provides an aseptic medium by which a surgical team member can manually adjust the operating room lamp during a surgical procedure, thereby preventing accidental or unknown incidental procedure, thereby preventing accidental or unknown incidental contamination. The non-disposable lamp handle includes an ergonomically designed grip handle and a locking/coupling assembly which couples the grip handle to the male component of the conventional surgical lamp. The sterile disposable handle cover is formed from a flexible sleeve closed at one end and having a relatively rigid collar formed about the opposite open end. By holding the sleeve just below the collar, the surgical team member can easily slide the handle cover over the grip handle to engage the locking/coupling assembly which holds the handle cover in a secure position. The surgical team member can easily disengage the handle cover after the surgical procedure in a similar fashion.

16 Claims, 3 Drawing Sheets

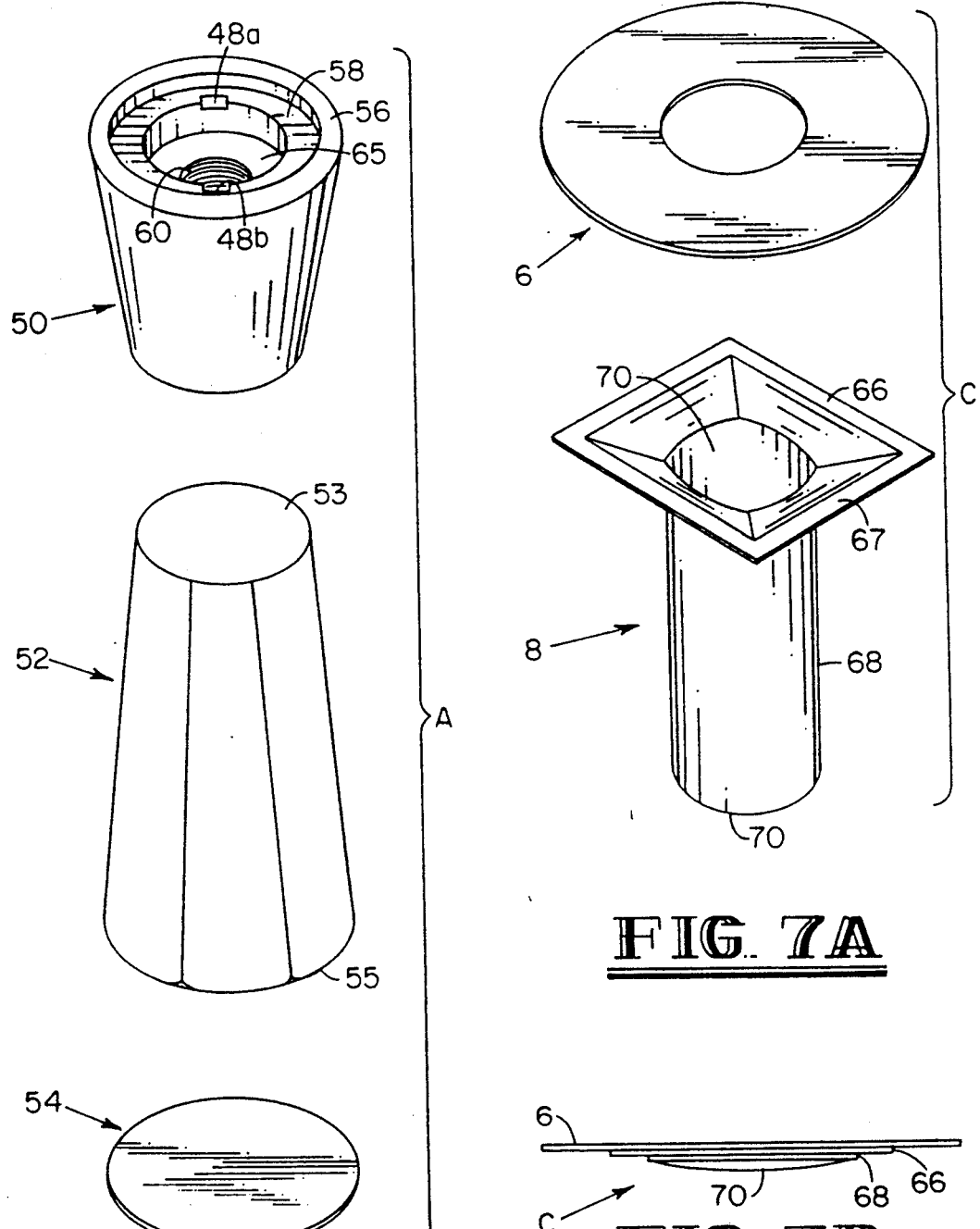

LAMP HANDLE COVER SYSTEM FOR SURGICAL LAMPS

This application is a continuation of application Ser. No. 07/585,290 filed Sep. 19, 1990, now U.S. Pat. No. 5,036,446, which is a continuation of application Ser. No. 07/235,978 filed Aug. 24, 1988, now abandoned.

BACKGROUND OF THE INVENTION

1. Field of Invention

The present invention relates to medical apparatus and, more particularly, to a semi-permanent, non-disposable surgical lamp handle and a sterile disposable lamp handle cover.

2. Description of the Prior Art

The continuing rise in costs of medical care and treatment despite the private efforts of health care facilities has resulted in the imposition of austere measures against health care facilities by both the federal government and third party payers (private health insurance payers, employers, etc.). As a result of these austerity measures, health care providers must take drastic action to control costs in order to survive.

In the past, health care institutions have identified their high cost areas and targeted them for increased cost control and productivity. The operating room has been one area with extremely high expenditures and corresponding high profitability. Therefore, institutions across the country have initiated programs designed to eliminate waste relating to operating room labor and supplies and to increase productivity, while striving to improve patient care.

One primary method for reducing wastes and keeping costs to a minimum in health care facilities is by converting from reusable to disposable sterile supplies. The use of disposable supplies is more critical than ever due to the increasing number of AIDS-related hospitalizations and the possible exposure of hospital patients or employees to the deadly virus. Policies such as the Center for Disease Control's "Universal Precautions" require that all blood and bodily fluids be treated as if infected.

Recently, there have been efforts to reduce costs and improve performance in the operating room by using disposable lamp handles or lamp handle covers instead of traditional, non-disposable lamp handles.

In the operating room, surgical lamps are typically located above the operating room table to provide illumination of the area about the surgical incision. Historically, adjustment of the surgical lamp by a surgical team member is achieved by the mounting of sterile surgical lamp handles onto the lamp prior to the commencement of the actual operative procedure. This sterile lamp handle provides a means for the surgeon or scrub nurse to adjust the lamp to illuminate the area of the surgical incision.

Traditionally, operating room surgical lamp handles have been non-disposable handles which are washed, wrapped and resterilized after each surgical procedure for the next day's operative case load. This is a costly, time-consuming and inefficient process. These costs have been amplified by the costs of storing the necessarily large number of non-disposable lamp handles. The bulkiness of the non-disposable lamp handles and the additional procedures necessary to resterilize it for the next operative procedure, increase the likelihood of accidental contamination.

Recently, there have been several attempts to remedy the problems associated with the conventional non-disposable lamp handle. These efforts fall into three different categories: the rigid disposable lamp handle, the rigid disposable lamp handle cover, and the flexible disposable lamp handle cover.

The rigid disposable lamp handles of recent design are typically composed of plastic and are an approximation of the rigid, resterilizible, non-disposable surgical lamp handle. Such disposable lamp handles have many of the same disadvantages as the non-disposable lamp handle. Due to the size of the disposable lamp handle, they are difficult to deliver to the sterile operative "set-up" table, and such deliveries may have to occur several times during an operative procedure. Such disposable lamp handles also store poorly on the sterile field. In addition, the disposable handle lacks structural integrity. Thus, such handles sometime flex during major movements of the lamp or become loose or separated from the male stud of the surgical lamp. Such disposable lamp handles also lack ergonomic design features, providing only a smooth cylindrical gripping surface for the surgical team member.

The rigid disposable lamp handle covers of recent design are typically mounted over the surgical lamp handle by sliding the rigid cover over the conventional non-disposable lamp handle. Such rigid disposable covers cannot be removed in a simple and easy fashion. This is primarily due to the frictional engagement of the handle cover with the handle, which is necessary for maintaining the handle cover in its proper position during use. It has been found that the quickest and surest method of removing the rigid cover is to remove the conventional non-disposable lamp handle which it is covering from the surgical lamp and then separating the rigid cover from the handle, thereby defeating a benefit of having the disposable cover. The size and lack of flexibility of the rigid cover also causes it to have many of the disadvantages of the conventional lamp handle in that it is difficult and time-consuming to deliver the rigid covers to the sterile operative "set-up" table. Such handle covers also store poorly on the sterile field and require too much space for the necessary inventory. Such handles also provide only a crude, smooth cylindrical grip and lack ergonomic design features.

Prior flexible disposable lamp handle covers are typified by a plastic cover which slips over a customized rigid non-sterilizable lamp handle. This flexible disposable cover is attached to the surgical lamp by sliding the lamp handle cover over the customized non-sterilized lamp handle previously mounted onto the surgical lamp and the positioning of the cover on the handle is maintained through both frictional and partial vacuum created forces.

It has been found that it is difficult to apply or remove such flexible disposable covers in the minimum amount of time required by operating room constraints. The cover is composed totally of flexible plastic having little structure, thereby increasing the difficulty of placing the cover over the customized lamp handle. Due to its flexible plastic composition, the cover tends to hold its packaged, folded form, thus increasing the difficulty in slipping the handle cover over the customized rigid lamp handle. Due to its tendency to maintain its packaged form, it may not adequately prevent against all accidental or unknown incidental contamination of the sterile glove hand of the surgical room operator.

Such prior art flexible covers also require a second step to complete the locking of the flexible disposable handle cover on the customized rigid lamp handle. This step consists of depressing the base of the cover in order to generate a partial vacuum which holds the cover in position. In order to relieve the vacuum during disengagement of the cover, the operator removing the cover must pull on the base. Due to the universal difficulty of placing any handle cover onto and removing such cover from the surgical lamp, which are commonly located above the operator's head, and the "light touch" mobility of the surgical lamp, such difficulties reduce many of the gains theoretically provided by a disposable cover. Since the customized handle used in conjunction with such disposable cover is also relatively short, the surgical room operator's effectiveness in gripping the handle through the handle cover is substantially reduced due to the lack of ergonomic design characteristics.

Another flexible light handle cover is exemplified by U.S. Pat. No. 4,559,671. This cover includes a grip portion defined by a first and second end. An end portion is integrally attached to the first end of the grip portion to form a hollow container suitable for sliding over the conventional lamp handle. A cone-shaped protector is connected about the second open end of the grip portion. This protector extends radially outward for protecting the hand of the operator from contacting portions of the surgical lamp. The cone-shaped protector includes a plurality of radially connected ribs to add mechanical strength to the protector. Normally these protector ribs are uniformally spaced. In addition, the grip portion includes a plurality of ribs integrally disposed on the interior side to provide frictional engagement with the lamp handle.

So far as known, there is yet to be provided for actual use, a lamp handle cover system which includes an ergonomically designed handle and a disposable handle cover which is capable of preventing accidental contamination and unknown incidental contamination of the surgical area, is easy to position over and/or remove from the lamp handle, and is also easy to store, handle, and dispose of in a safe, efficient and cost effective manner.

It is an object in the present invention to supply a non-disposable, semi-permanent lamp handle and its accessory component, a sterile disposable semi-flexible handle cover, which markedly improves the efficiency and performance of adjusting lamps in the operating room, while maintaining a high level of sterile technique, thereby reducing the costs of providing surgical services.

Another object of this invention is to provide an anthroprometrically designed lamp handle which can be easily mounted onto the standardized male component of conventional surgical lamps.

Another object of this invention is to provide a lamp handle having a locking mechanism for insuring that the handle cover is securely mounted about the lamp handle.

Another object of the invention is to provide a disposable surgical lamp handle cover which can be readily presterilized, compactly packaged, and easily disposed of in a safe manner.

SUMMARY OF THE INVENTION

Briefly, the present invention is a new and improved lamp handle cover system for providing aseptic means to manipulate a surgical lamp. The system includes a semi-permanent handle for manipulating the surgical lamp, a disposable semi-flexible cover for covering the semi-permanent handle to provide a sterile gripping surface for an operator to manipulate the lamp, and a locking mechanism for locking the disposable handle cover in position about the handle.

The handle includes a lower conical portion having a base end and a truncated apex end suitably sized for a hand to grasp the handle, an upper inverted conical portion having a base end and a truncated apex end integrally connected to the truncated apex end of the lower conical portion and a coupling-assembly for coupling the base end of the upper conical portion of the handle to the surgical lamp. The locking assembly is mounted about the coupling assembly.

The disposable cover includes a sleeve of plastic material open in one end and closed in the other end and a collar of rigid material connected about the open end of the sleeve. Preferably, the sleeve includes a flange portion integrally formed about the open end thereof which may be attached to the collar. Preferably, the lower conical portion of the handle a hexahedral-shaped gripping surface and a suitable diameter to allow the thumb and forefinger of a hand gripping the lower portion to overlap.

BRIEF DESCRIPTION OF THE DRAWINGS

FIG. 6 is an exploded perspective view of the grip handle of the handle assembly.

FIG. 7a is an exploded perspective view of the handle cover.

FIG. 7b is a perspective view of a folded handle cover.

DESCRIPTION OF THE PREFERRED EMBODIMENT

Figure 1:
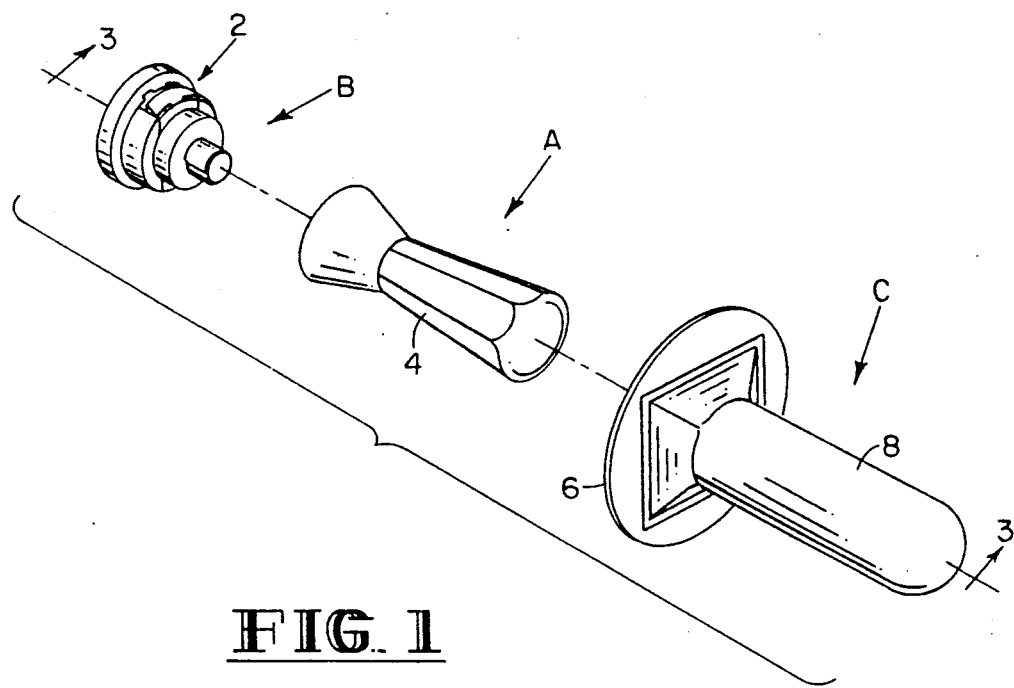
FIG. 1 is a perspective view of the handle cover system embodying my invention.

In the drawings, the light handle cover system A of the present invention comprises a rigid, semi-permanent, non-disposable surgical lamp handle assembly B and a sterile disposable handle cover C to provide new and improved aseptic means to adjust a conventional surgical lamp (not shown) during an operative procedure in the operating room. The system A prevents accidental or unknown incidental contamination of the sterile gloved hand of the surgical team member having responsibility for adjusting the surgical lamps during a surgical procedure to illuminate the critical surgical area.

The non-disposable lamp handle B includes a coupling/locking assembly 2 and a novel ergonomic grip handle 4. The grip handle 4 of the present invention is first screwed into the coupling/locking assembly 2 to form the semi-permanent non-disposable lamp handle B. The coupling/locking assembly 2 of the lamp handle is then screwed onto the male component of the conventional surgical lamp in substantially the same manner in which the conventional resterilizable lamp handle is attached.

The disposable light handle cover C includes a rigid sleeve collar 6 and a flexible sleeve-type cover 8 which is closed at one end and open at a second end. The rigid sleeve collar 6 is joined to the flexible sleeve to form the disposable handle cover C. The disposable handle cover C can then be easily fitted over the lamp handle B and locked into position by the coupling/locking assembly 2 thereof in a manner described in more detail below.

Figure 2A:
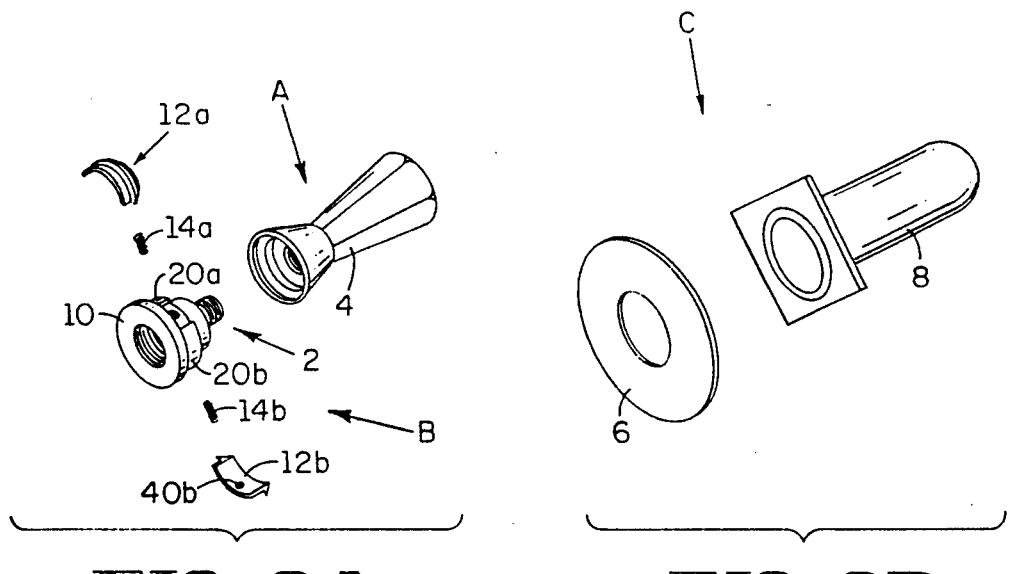
FIGS. 2a and 2b are exploded perspective views of the handle and handle cover, respectively.
Figure 2B:
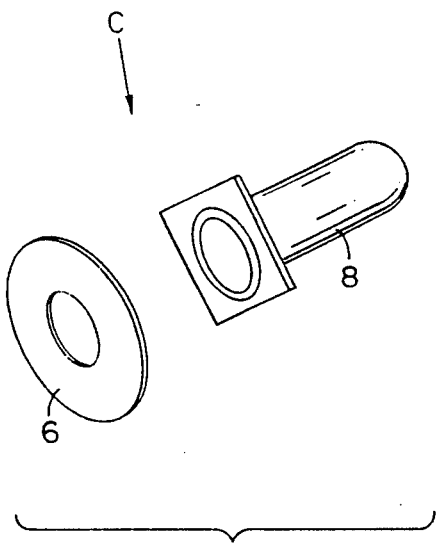

Referring to FIGS. 2A and 2B, the lamp handle assembly B and handle cover C is shown in exploded form. The novel coupling/locking assembly 2 includes a snap ring hub 10 about which movable snap rings 12a and 12b are mounted in movable positions about the center portion of the snap ring hub and which is biased into a locked position when the sleeve collar 6 of the handle cover C is positioned about the snap rings in a manner described in more detail below.

Figure 3A:
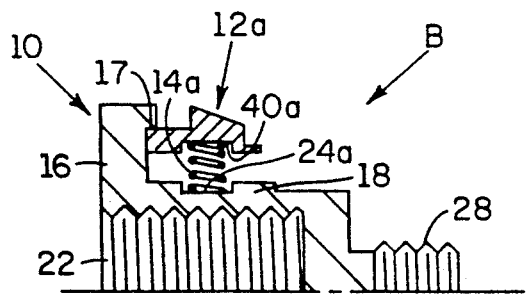
FIGS. 3a and 3b are sectional views along line 3—3 of FIG. 1 showing the coupling/locking assembly.
Figure 3B:
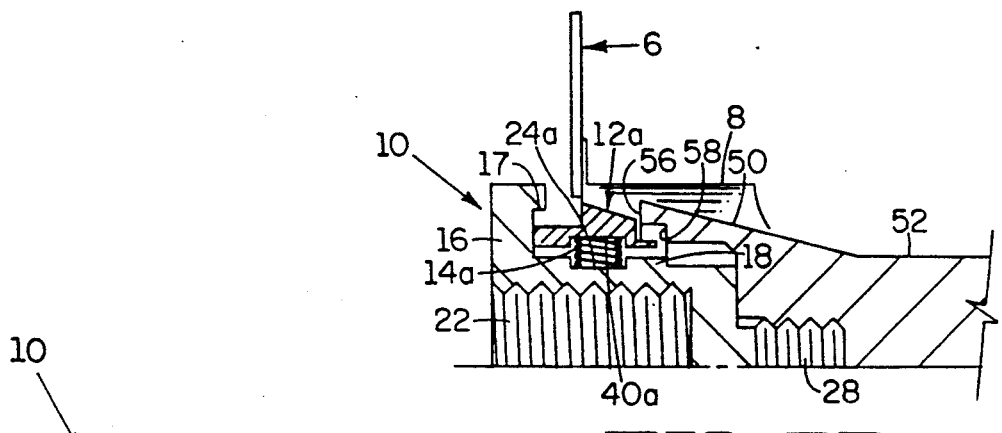
Figure 4:
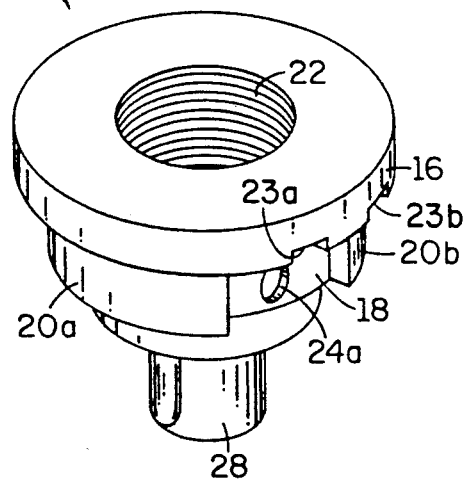
FIG. 4 is a perspective view of the snap ring hub of the coupling/locking assembly.

As shown in FIGS. 3 and 4, the snap ring hub 10 comprises a series of integrally formed cylindrical portions of varying diameters which serves both as a coupling mechanism for connecting the grip handle 4 to the threaded stud of the conventional surgical lamp and as a primary component of the locking mechanism for holding the semi-flexible handle cover C in a secure position.

The hub 10 has an upper cylindrical portion 16 having an outer diameter suitably sized to maintain the structural integrity of the snap ring hub 10. Thus the portion 16 serves as a structural support for the remainder of the coupling/locking assembly 2.

The snap ring hub 10 also has a middle portion 18 having wedge segments 20a and 20b integrally formed on diametrically opposite sides of the middle portion 18. Such wedge segments provide adjacent sliding surfaces for the movable snap rings 12a and 12b, thereby preventing rotation or non-alignment of the movable snap rings relative to the middle portion of the hub 10. A groove 17 is formed in the surface by the intersection of the upper portion 16 and middle portion 18 to function as a stop ring bracket for holding the snap rings in position about the middle portion of the hub.

A threaded opening 22 having a suitable thread design is formed through the first and second portions of the hub 10 in order for the hub 10 to be secured on the existing threaded stud of the conventional surgical lamp.

Two pairs of alignment slots 23a and 23b are formed on diametrically opposite positions of the upper cylindrical portion 16 to prevent the rotation or non-alignment of the movable snap springs 12 during placement and removal of the disposable light handle cover C. The middle cylindrical portion 18 also has at least two recessed openings 24a and 24b formed therein, preferably at 180 degrees from each other, for accepting compression springs 14a and 14b.

In assembling the locking assembly 2, the compression rings 14a and 14b, respectively, are mounted into recess openings 24a and 24b, respectively, prior to the placement of the movable snap rings 12a and 12b, respectively, about the hub 10. The compression springs 14 provide necessary compressional forces for the snap rings 12 to be moved between the position shown in FIG. 3A and the position shown in FIG. 3B when pressure is applied to snap ring 12.

The snap ring hub 10 has a lower portion formed into a stud 28 which provides a coupling mechanism for joining the locking/coupling assembly 2 to the ergonomically designed grip handle 4, as shown in FIG. 2. The stud 28 may be threaded. Preferably, the stud 28 is a "press fit" stud which is bonded to the hub 10 with a conventional adhesive.

Figure 5:
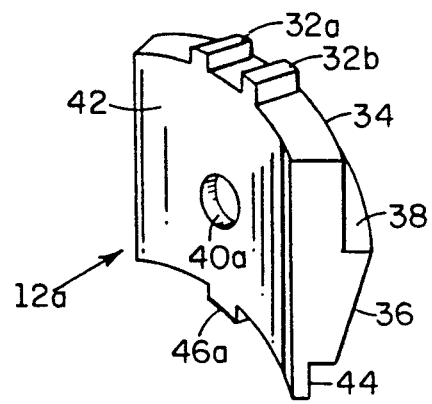
FIG. 5 is a perspective view of the snap ring of the locking assembly.

As shown in FIG. 5, each of the snap rings 12a and 12b comprise a semi-cylindrical form of integrated design having parallel alignment tabs 32. The alignment tabs 32a and 32b are of suitable dimensions and location to allow mating of the tabs 32 with the parallel alignment slots 23a and 23b formed in the upper portion of the hub 10. When the movable snap rings 12a and 12b are placed into a position about the hub 10 so that the tabs 32 are aligned with the slots 23, rotation or non-linear movement of the movable snap rings relative to the hub 10 is prevented during either placement on or removal of the disposable light handle cover C.

The movable snap rings 12 also have an upper cylindrical surface 34 and a conical surface 36, the base of which has a larger diameter than that of the upper cylindrical surface 34, thereby creating a semicircular alignment stop 38 for the disposable cover C when the disposable cover C is moved upward across the surface 36.

Circular recesses 40a and 40b are also formed on the inner surface 42 of the movable snap rings 12 and aligned with corresponding recess openings 24a and 24b in the hub 10 to provide a housing for the compression springs 14a and 14b. A lower wedge portion 44 of the snap ring 12 is sized to fit the alignment stop formed by the intersection of the concentric openings of varying diameter formed in the upper inverted truncated cone portion of the grip handle 4. Lower alignment tabs 46a and 46b are formed at the lower end of the wedge portion 44. Tabs 46 mate with alignment slots 48a and 48b formed in the inner surface of the first concentric opening formed in the upper inverted truncated cone portion of the handle 4. The placement of the alignment tabs 46 of the snap rings into the alignment slots 48 of the grip handle prevent the rotation or non-linear movement of the movable snap rings 12a and 12b during placement on and removal of the disposable light handle cover C from the locking assembly 2.

With respect to the interaction of the movable snap rings 12 relative to the snap ring hub 10, two pairs of compression springs 14a and 14b are inserted into the two pairs of openings formed in the middle portion of the snap ring hub 10. Then, the movable snap rings 12a and 12b are positioned about the circumference of the middle portion of the hub 10 such that the pair of compression springs 14a and 14b fit into the pair of recess openings 40a and 40b formed in the snap rings. The rings 12 are then held in position by the stop ring bracket portion of the hub 10 and the stop ring portion formed by first and second concentric openings in the upper inverted truncated cone portion of the grip handle 4.

In summary, the movable snap rings 12a and 12b are maintained in their position by virtue of the compression springs 14, the parallel alignment slots 23, the upper alignment tabs 32, the lower alignment tabs 46 and the diametric alignment slots 48, as illustrated in FIGS. 3a and 3b.

When the movable snap rings 12 are in a locked position the movable snap rings form a circular locking mechanism having a diameter slightly larger than the interior diameter of the cylindrical sleeve collar of the disposable handle cover C, thereby allowing for placement and locking of the disposable light handle cover C.

When in the unlocked position shown in FIG. 3b, the movable snap rings 12 form a circular locking mechanism having a diameter slightly less than the inner diameter of the sleeve collar of the handle cover C, thereby allowing for removal of the disposable light handle cover C. The light handle cover is removed by manually depressing the movable snap rings 12 and pulling the cover C away in the downward direction from the locking assembly 2.

Prior art devices for holding a handle cover into position around a semi-permanent non-disposable handle utilized either utilized frictional forces between the cover and the handle or utilized a combination of frictional forces between the cover and handle and partial vacuum forces. In comparison, the locking assembly 2 of the present invention provides greater performance in both speed and effectiveness with respect to placing on and removing the cover from the lamp handle without the use of such frictional or suction forces. In addition, with the locking assembly of the present invention, a sterile gripping surface is better maintained. The locking assembly 2 also reduces the amount of time necessary to place and remove the cover C.

Referring to FIG. 6, the essential features of the grip handle 4 are shown in exploded form. The grip handle 4 includes an upper inverted truncated cone portion 50, a lower truncated cone portion 52, and elliptical base portion 54.

The upper inverted truncated cone 50 includes a portion 56 having an inner diameter larger than the inner diameter of a second collar portion 58, which in turn has a larger inner diameter than a threaded opening 60. The threaded opening 60 is designed to mate with the threaded stud portion of the snap ring hub 10. The surface formed by the transition from the first portion 56 and the collar portion 58 functions as a stop ring to maintain the position of the compression-spring forced movable snap rings 12 in a locked position.

Lower alignment slots 48a and 48b are formed in the collar portion 58, preferably at 180 degrees from each other. Such alignment slots are designed to fit into the corresponding lower alignment tabs 46 formed in the snap ring hub 10 when the lower portion of the snap ring hub 10 is inserted into the opening formed by the inner diameter of the portion 58. The insertion of the lower alignment tabs 46 into the alignment slots prevents the rotation or non-linear motion of the movable snap rings 12 during placement and removal of the upper truncated cone portion 50 of the handle cover C over the locking assembly 2.

The grip portion 52 of the grip handle 4 has a hexagonal configuration for a firmer grip when manipulating the surgical lamp. The hexagonal profile grip is similar to the shape of the hand when it is in a gripping position, thereby providing a comfortable, secure grip to manipulate the surgical lamp handle. The hexagonal profile grip of the handle also provides gripping surfaces with which to rotate the lamp.

Preferably, the diameter of the grip portion 52 at the truncated apex 53 is approximately 1.15 inches, thereby allowing an overlap of the thumb and forefinger. Preferably, the diameter of the grip portion at the base 55 is approximately 1.85 inches. The minimum diameters for the truncated apex and base depend upon the amount of forces exerted. For example, if 25 pounds or more are exerted, a minimum of ¾ inches is needed.

A suitable length of the grip portion is approximately 3.5 inches. It should be noted that other lengths may be used so long as the maximum diameter at the base 55 of the grip portion 52 does not greatly exceed 1½ inches and the length of the hand grip is at least 3¾ inches to accommodate the full breadth of the hand.

Joined in a smooth merge to the lower truncated cone portion 50 is the elliptical base portion 54 of the grip handle. The elliptical base is formed by joining a hemi-oblated ellipsoid to the end of the truncated cone.

The grip handle is preferably manufactured from a suitable strong, durable, lightweight plastic material, such as polycarbonate plastic using injection molding techniques.

The ergonomically designed grip handle 4 of the present invention provides several advantages over prior art devices. The grip is conical so that a variety of hand sizes will conform to the grip. For example, smaller than normal hands can comfortably grip the smaller diameter portion of the grip handle, whereas larger than normal hands can comfortably grip the larger diameter portion of the grip handle. Additional advantages are obtained due to the distribution of forces during gripping. Traditionally, surgical lamp handles have had circular profiles or cylindrical grips. With the hour glass shape, the gripping forces lock the hand into a grip. This reduces the total forces necessary to maintain the hand in a gripped position around the handle. The forces are also directed into the handle 4 and not tangentially along the disposable lamp handle cover C. The ability to move the lamp through the handle assembly B is not based on frictional forces, but on static structural forces. Even gloved hands made slippery with body fluids can easily manipulate the surgical lamp. Prior art lamp handles addressed the issue of ergonomics in only the crudest form. For example, they were only round profile handles and had less than the desired length of 3¾ inches.

With respect to structural integrity, the rigid resterilizable handle of the present invention maintains its placement on the surgical lamp in an acceptable repeatable fashion.

Referring to FIG. 7a, the features of disposable light handle cover C are shown in exploded form. The disposable lamp handle cover C comprises a rigid sleeve collar 6 and a flexible cylindrical sleeve 8.

The outer diameter of the sleeve collar 6 is sufficiently large, five inches for example, so that the sterile gloved hand of the surgical team member, when grasping the handle, will not accidentally touch an unsterilized portion of the surgical lamp thereby causing incidental contamination.

The inner diameter of the sleeve collar 6 is suitably sized so that it engages the movable snap rings 12 of the locking assembly 2 and forces the compression springs downward until the collar 6 slips over the alignment stop 38 (see FIG. 5).

The sleeve collar 6 can be formed from plastic material using injection molding manufacturing techniques. The collar 6 is sufficiently thick to provide the rigidity and the material composition necessary for efficient heat sealing of the disposable light handle cover 6. The relative rigidity of the sleeve collar provides a rigid supporting structure for easy engagement and disengagement with the locking surface of the movable snap rings 12. Preferably, the thickness and composition of the cylindrical sleeve collar 6 is kept within a range which provides the appropriate balance between rigidity, heat sealability and ease of manufacture.

The second major component of the disposable handle cover C is a flexible sleeve 8, preferably constructed of a suitable thin plastic material so that the surgical team member can easily and securely grip the underlying grip handle 4 for positioning the surgical lamp. As shown in FIG. 7b, the thin, flexible material also allows the cover C to be compactly packaged for ease in storing, transporting and handling.

The essential features of the first embodiment of the flexible sleeve 8 are shown in FIG. 7. Preferably, the flexible sleeve 8 includes a lip or flange portion 66, which is integrally or unitarily formed with a sleeve portion 68 having an opening 70 in the end to which the flange portion 66 is affixed and a closed end 70. The closed end preferably has a hemi-oblated-ellipsoidal configuration so that it conforms to the shape of the grip handle.

Preferably, the flange or lip portion 66 is square although other configurations may be suitable. The flange portion 66 is sufficiently large to provide a suitably large horizontal surface for heat sealing the sleeve collar 6 to the sleeve cover 8. For example, the flange portion 66 should be suitably large such that the heat seal line 67 formed by the conventional thermoforming machine is suitably spaced between the outer ends of the flange portion 66 and the opening 70 of the sleeve portion 68. In an alternative embodiment, the sleeve portion of the sleeve 8 may be a gussetted folded bag of suitable plastic material.

The relatively rigid heat sealable sleeve collar 8 is composed of a suitable plastic material, such as polyethylene. The sleeve collar 6 may be manufactured using either an injection molding process or a die press process.

Although a wide variety of plastic materials may be suitable for sleeve 8, preferably the sleeve is made of a 30 mil coextrusion of laminated polyethylene laminate or a 30 mil coextrusion of laminate ethylene-vinyl acetate of 3-10 mil polyethylene layers. Such a coextrusion is beneficial for deep draw thermoforming, heat sealing the flexible sleeve 8 to the collar 6 and for providing the maximum amount of flexibility for package folding and actual use. It should be noted, however, that any other materials that are compatible with deep draw thermoforming, heat sealing processes and flexibility are acceptable.

The flexible sleeve 8 may be manufactured using a variety of conventional thermoforming techniques including straight vacuum forming, drape forming, match mold forming, plug assist, or a combination of the above.

The sleeve collar 6 may be affixed to the flexible sleeve 8 by several different techniques. One method of affixing the collar 6 to the sleeve 8 is to use a thermal impulse heat seal process or straight seal welding. Alternatively, a radio frequency heat sealing process can be used. Furthermore, the sleeve 8 and the collar 6 can be assembled either using a chemically bonding adhesive or a mechanically bonding adhesive. Such manufacturing techniques are well-known by persons ordinarily skilled in the art. Preferably, the process for affixing the subcomponents of the disposable handle cover C uses a separate thermoforming station for manufacturing the flexible sleeve cover 8 and a semi-automatic heat seal process with a manual load of sleeve 8 and collars 6 for affixing the flexible sleeve 8 and the sleeve collar 6.

Alternatively, the manufacturing process for the cover C may be an integrated manufacturing process, rather than the assembly of the two subcomponents by a heat seal or chemical bonding process. For example, a sheet of suitable plastic material may be thermoformed to form the sleeve. The thermoformed sleeve may then be round die punched using a die with a diameter equivalent to the outer diameter of the cylindrical sleeve collar 8. The advantages of the integrated manufacturing process consist of a major reduction in material usage and an elimination of the attachment process for attaching the sleeve and collar. This process drastically reduces the time and cost of manufacturing.

The foregoing disclosure and description of the invention are illustrative and explanatory thereof, and various changes in the size, shape and materials, as well as in the details of the illustrated construction, may be made without departing from the spirit of the invention.

I claim:

1. A lamp handle cover system for providing aseptic means to manipulate a surgical lamp, comprising:
    a handle for manipulating the surgical lamp;
    a disposable cover for covering said handle to provide a sterile gripping surface for an operator to manipulate the lamp:
        a sleeve portion of flexible material having an open first end and a second end; and
        a collar portion of relatively rigid material, said collar means being connected around the edge of the opening therein to the first end of the sleeve portion such that said opening in said collar means and the open first end of said sleeve portion are substantially aligned; and
    locking means for locking the cover to the handle, said locking means comprising means on said handle for lockingly engaging the inner edge of said collar portion of said disposable handle cover when said cover is moved into operative position about said handle.

2. The apparatus of claim 1 wherein said locking means includes a biasing means for biasing said locking means toward the locked position.

3. The apparatus of claim 2 wherein said locking means comprises a hub and a ring means about said hub with said biasing means biasing said ring means toward the locked position.

4. A handle for manipulating a pivotal lamp, comprising:
    means for gripping the handle;
    means for coupling the handle to the lamp; and
    means affixed to the handle for locking a disposable handle cover into position over the handle to prevent contamination of the hand gripping the handle;
    said locking means including a biasing means for biasing said locking means toward the locked position.

5. The apparatus of claim 4 wherein said locking means comprises a hub and a ring means about said hub with said biasing means biasing said ring means toward the locked position.

6. The apparatus of claim 5, wherein said coupling means includes said locking means, said coupling means further including means for connecting the handle to a conventional surgical lamp.

7. The apparatus of claim 4 wherein said handle comprises:

a first conical portion having a base end and a truncated apex end suitable for a hand to grip the lamp handle, whereby the conical shape permits a variety of hand sizes to firmly grip the handle; and an inverted conical portion having a base end and a truncated apex end connected to said truncated apex end of said first conical portion.

8. The handle of claim 7, wherein:

the first conical portion has a hexahedral gripping surface and its base end has an elliptically shaped surface.

9. The handle of claim 8, wherein:

the diameter of the upper truncated end of the first conical grip portion is sufficiently small to allow the thumb and forefinger of a hand gripping said first portion to overlap.

10. The handle of claim 7, wherein:

the diameter of the base end of the first conical grip portion is larger than the optimum diameter for the normal hand grip.

11. A disposable lamp handle cover for the handle of a surgical lamp for providing a sterile surface for an operator to manipulate the lamp, comprising:

a sleeve portion of flexible material with an open end and a closed end, forming a void which is sufficiently large to allow its mounting on the handle without significant friction or other form of resistance; and a relatively rigid collar portion connected about the opening therein to said open end of said sleeve portion so that said collar opening and said open end of said sleeve portion are substantially aligned; whereby the operator can easily mount the cover on the handle, firmly grip the handle through the cover to manipulate the lamp, and easily remove the cover from the handle with one hand.

12. The handle cover of claim 11, wherein:

said sleeve portion is formed from a flexible aseptic barrier material.

13. The handle cover of claim 12, wherein:

said collar portion is formed from a relatively rigid aseptic barrier material and has an outer diameter larger than the diameter of the portion of the lamp housing to which the handle is connected.

14. The handle cover of claim 13, wherein the inner edge of said collar portion is designed to cooperate with a locking means on a lamp handle.

15. A lamp handle cover system for providing aseptic means to manipulate a surgical lamp, comprising:

a handle for manipulating the surgical lamp which includes:

a first conical portion having a base end and a truncated apex end suitably sized for a hand to grasp the handle;

an inverted conical portion having a base end and a truncated apex end integrally connected to the truncated apex end of the first conical portion; and coupling means mounted on said base end of said inverted conical portion with means to connect said handle to the surgical lamp;

a disposable cover for covering said handle to provide a sterile gripping surface for an operator to manipulate the lamp which includes;

a sleeve portion of flexible material having an open first end and a second end; and a collar portion of relatively rigid material, said collar portion connected to the first end of the sleeve portion around the opening therein such that said collar opening and the open first end of said sleeve are substantially aligned.

locking means positioned about said coupling means to lockingly engage the inner edge of said collar for locking said disposable handle cover in an operative position, to provide a sterile gripping surface about the handle for an operator to manipulate the lamp.

16. The lamp handle cover system of claim 15 wherein said coupling means includes a hub with ring means and biasing means mounted around said hub, said biasing means forcing said ring means into a locked position to form said locking means.

* * * * *

UNITED STATES PATENT AND TRADEMARK OFFICE
CERTIFICATE OF CORRECTION

PATENT NO. : 5,188,454

DATED : Feb. 23, 1993

INVENTOR(S) : Quintanilla, et al.

It is certified that error appears in the above-identified patent and that said Letters Patent is hereby corrected as shown below:

Title page,
    item [63], delete "August 27, 1988" and insert -- August 24, 1988 --.

Signed and Sealed this

Twelfth Day of September, 1995

Attest:

BRUCE LEHMAN

*Attesting Officer*      *Commissioner of Patents and Trademarks*